US010765482B2

(12) United States Patent
Hastings

(10) Patent No.: US 10,765,482 B2
(45) Date of Patent: *Sep. 8, 2020

(54) CATHETER GUIDANCE OF EXTERNAL ENERGY FOR RENAL DENERVATION

(71) Applicant: Boston Scientific Scimed, Inc., Maple Grove, MN (US)

(72) Inventor: Roger Hastings, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 41 days.

This patent is subject to a terminal disclaimer.

(21) Appl. No.: 15/080,340

(22) Filed: Mar. 24, 2016

(65) Prior Publication Data
US 2016/0206385 A1 Jul. 21, 2016

Related U.S. Application Data

(63) Continuation of application No. 13/295,182, filed on Nov. 14, 2011, now Pat. No. 9,326,751.
(Continued)

(51) Int. Cl.
A61B 8/00 (2006.01)
A61B 34/20 (2016.01)
A61B 8/08 (2006.01)
A61B 8/12 (2006.01)
A61B 17/22 (2006.01)
(Continued)

(52) U.S. Cl.
CPC .............. A61B 34/20 (2016.02); A61B 6/032 (2013.01); A61B 8/0841 (2013.01); A61B 8/12 (2013.01); A61B 8/4488 (2013.01); A61B 17/2202 (2013.01); A61B 90/39 (2016.02); A61N 7/02 (2013.01); A61B 8/445 (2013.01); A61B 2017/00106 (2013.01); A61B 2018/00404 (2013.01); A61B 2018/00434 (2013.01); A61B 2018/00511 (2013.01); A61B 2034/2051 (2016.02); A61B 2034/2063 (2016.02); A61B 2090/378 (2016.02); A61B 2090/3788 (2016.02); A61B 2090/3929 (2016.02); A61B 2090/3958 (2016.02); A61B 2090/3966 (2016.02); A61N 2005/1051 (2013.01); A61N 2005/1058 (2013.01); A61N 2007/003 (2013.01); A61N 2007/0052 (2013.01)

(58) Field of Classification Search
CPC combination set(s) only.
See application file for complete search history.

(56) References Cited

U.S. PATENT DOCUMENTS

| 5,240,003 A * | 8/1993 | Lancee | A61B 8/12 310/162 |
| 8,167,805 B2 * | 5/2012 | Emery | A61B 50/13 600/437 |
| 2008/0287783 A1 * | 11/2008 | Anderson | A61B 5/062 600/429 |

* cited by examiner

Primary Examiner — Joseph M Santos Rodriguez

(57) ABSTRACT

An in vivo apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. An ex vivo apparatus includes an arrangement configured to localize the energy guide apparatus within the renal artery, and an energy source configured to direct ablative energy to target tissue located a predetermined distance from the localized energy guide apparatus. The target tissue includes perivascular renal nerve tissue adjacent the renal artery.

20 Claims, 13 Drawing Sheets

Related U.S. Application Data

(60) Provisional application No. 61/414,735, filed on Nov. 17, 2010.

(51) Int. Cl.
| | | |
|---|---|---|
| *A61N 7/02* | (2006.01) | |
| *A61B 90/00* | (2016.01) | |
| *A61B 6/03* | (2006.01) | |
| *A61B 17/00* | (2006.01) | |
| *A61B 18/00* | (2006.01) | |
| *A61N 5/10* | (2006.01) | |
| *A61N 7/00* | (2006.01) | |

# CATHETER GUIDANCE OF EXTERNAL ENERGY FOR RENAL DENERVATION

RELATED PATENT DOCUMENTS

This application is a continuation of U.S. Ser. No. 13/295,182, filed Nov. 14, 2011; and claims the benefit of Provisional Patent Application Ser. No. 61/414,735, filed Nov. 17, 2010, to which priority is claimed pursuant to 35 U.S.C. § 119(e) and which are hereby incorporated herein by reference.

SUMMARY

Embodiments of the disclosure are directed to apparatuses and methods for guiding externally generated ablative energy to target tissues within the body. Embodiments of the disclosure are directed to apparatuses and methods for guiding externally generated ablative energy to target tissues within the body using an in vivo energy guide apparatus. Various embodiments are directed to apparatuses and methods involving localizing an energy guide apparatus positioned within a target vessel, such as a renal artery, and directing externally generated ablative energy to target tissue of the body, such as perivascular renal nerve tissue.

In accordance with various embodiments, an in vivo apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. An ex vivo apparatus includes an arrangement configured to localize the energy guide apparatus within the renal artery, and an energy source configured to direct ablative energy to target tissue located a predetermined distance from the localized energy guide apparatus. The target tissue includes perivascular renal nerve tissue adjacent the renal artery.

According to some embodiments, an apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. The energy guide apparatus is configured to generate an energy beacon that facilitates locating of the energy guide apparatus within the renal artery. An external system includes a receiver configured to receive the energy beacon, a processor configured to localize the energy guide apparatus based at least in part on the received energy beacon, and an energy source configured to direct ablative energy to target tissue located a predetermined distance from the localized energy guide apparatus. The target tissue includes perivascular renal nerve tissue.

According to other embodiments, an in vivo apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. The energy guide apparatus includes a magnetic field generator configured to generate a rotating magnetic field, and an ultrasound generator configured to generate a rotating beam of acoustic energy. A support structure is provided at the distal end of the shaft and transformable between a low-profile introduction configuration and a deployed configuration. The support structure serves to center the energy guide apparatus within the renal artery when in the deployed configuration. An ex vivo apparatus includes an array of magnetic field sensors configured to sense the rotating magnetic field, and an ultrasound transducer array configured to detect the rotating beam of acoustic energy. A processor is configured to localize the energy guide apparatus based at least in part on the sensed rotating magnetic field and the detected rotating beam of acoustic energy. An energy source is configured to direct ablative energy to target tissue located a predetermined distance from the localized energy guide apparatus. The target tissue includes perivascular renal nerve tissue.

In accordance with various embodiments, a method involves localizing an energy guide apparatus positioned within a renal artery of a patient, and directing ablative energy to target tissue located a predetermined distance from the localized energy guide apparatus. The target tissue includes perivascular renal nerve tissue.

According to some embodiments, a method involves generating, at an energy guide apparatus positioned within a patient's renal artery, a rotating magnetic field. The method also involves generating, at the energy guide apparatus, a rotating beam of acoustic energy. The method further involves sensing, externally of the patient, the rotating magnetic field, detecting, externally of the patient, the rotating acoustic energy beam, and localizing the energy guide apparatus based at least in part on the sensed rotating magnetic field and the detected rotating acoustic energy beam.

These and other features can be understood in view of the following detailed discussion and the accompanying drawings.

DETAILED DESCRIPTION

Figure 1:
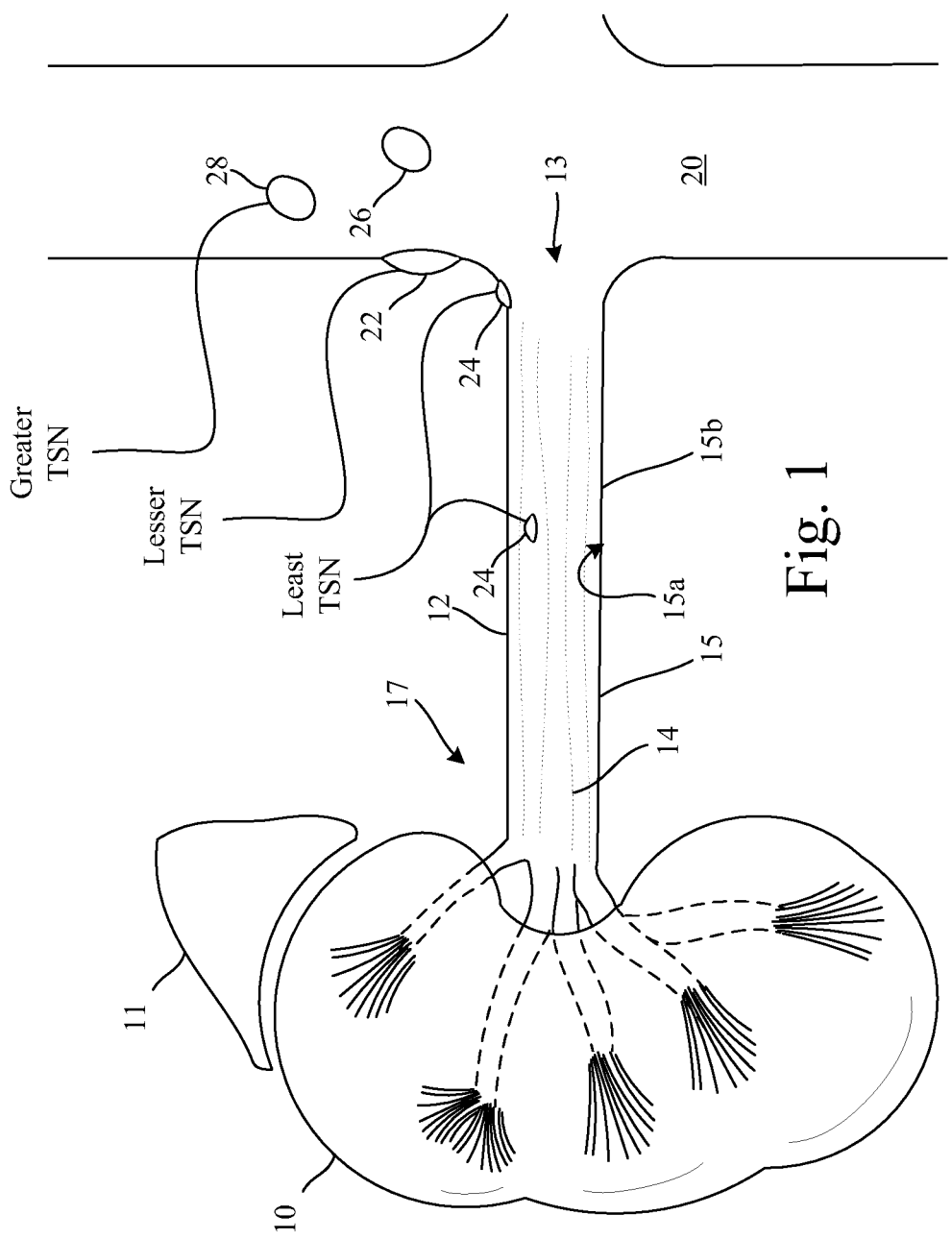
FIG. 1 is an illustration of a right kidney and renal vasculature including a renal artery branching laterally from the abdominal aorta.

Renal denervation has been performed as a therapy for refractory hypertension using surgical and radiofrequency (RF) ablation interventions. Surgical denervation is considered too invasive and too morbid in the modern era of drug therapy. RF ablation of the renal nerves using an RF tip catheter placed against the wall of the renal artery is a promising new technology. However, it unavoidably does some damage to the wall of the renal artery, with side effects that may not be fully known until the procedure becomes widely performed.

External beam ablation of the renal nerves has the potential to avoid damage to the adjacent artery wall, providing that the beam can be targeted precisely. Since the intima and media of the artery wall may be within a few millimeters of the renal nerves, targeting of an external beam must be very precise to avoid damage. According to various embodiments, a position and orientation system of the disclosure is capable of sensing the position of a target within the body to within one mm center-to-center of the actual position of the target. While renal blood flow does cool the artery wall, the external beam generates heat on the outside surface of the artery at the location of the renal nerves, with no heat deposited directly on the inside artery wall surface.

Embodiments of the disclosures are directed to a catheter apparatus configured to precisely locate the renal nerves and guide the external beam ablation. According to various embodiments, a micro-motor driven intravascular ultrasound (IVUS) catheter is placed into the renal artery proximate a site chosen for ablation of adjacent renal nerves. An array of acoustic transducers is placed against the patient's skin adjacent the region of the renal artery. The IVUS catheter projects a conical beam of ultrasound energy that rotates in a plane perpendicular to the catheter long axis. The IVUS beam is received by the transducers in the external array, to identify the location of the IVUS catheter residing in the renal artery.

The IVUS catheter may be centered in the renal artery, for example by inflating a balloon around the imaging core. The diameter of the renal artery may be determined from the IVUS image, or from quantitative angiography of the renal artery, and this information may be used to direct the external beam of ultrasound to sites that are adjacent to the artery wall, but located a short distance away from the inside of the artery wall. Recent studies of human cadavers have revealed that renal nerves can lie as close as about 0.5 mm from the lumen of a renal artery, with most renal nerves lying within about 3.5 mm of the artery lumen. Other structures of the body, such as bowel, can be as close as 4 mm from the artery wall. As a general rule, a relatively safe target zone for performing renal denervation in accordance with embodiments of the disclosure would be a zone between about 0.5 to 3.5 mm from the lumen wall of a renal artery. The size of the ablation zone considered to be safe is, of course, highly dependent on the anatomy of a particular patient. As is discussed below, human renal nerves have been found lying out as far as about 7 mm from the lumen wall of a renal artery. As such, the size of the ablation zone can be as deep as between 0.5 and 7 mm from the lumen wall of a renal artery.

According to some embodiments, the magnetic field of a magnet used to rotate a mirror of the IVUS catheter is sensed by an array of external magnetic sensors that are synchronized to the magnet rotation. The magnetic sensor data may be used to precisely localize the IVUS transducer (e.g., a component of the IVUS transducer, such as a rotating magnet of a micro-motor) relative to a fixed external reference frame of the external magnetic sensors, which is in a measured relationship relative to a reference frame of an external energy source, such as a high-intensity focused ultrasound (HIFU) array. Localizing the IVUS transducer preferably involves determining the Cartesian coordinates and orientation angle of the IVUS transducer. Data from the rotating IVUS beam and the localization of the rotating magnet are combined to precisely guide a phased array ultrasound ablation beam to perivascular renal nerve tissue adjacent the renal nerve. Ablation is performed at points around the renal artery. Two or more locations of the external array may be needed to complete a circumferential ablation. The IVUS catheter may image adjacent tissue to assess the extent and location of the ablation.

Other embodiments include guidance of an external beam of x-ray or gamma-ray radiation. According to these embodiments, a radiopaque marker on the catheter, for example the stator of an IVUS micro-motor, may be used to locate the catheter tip, for example using an external CT scanner. A second, real time localization is preferably provided by sensing the rotating magnetic field of the micro-motor. The CT scan may be displayed and co-registered with the magnetic localization system and external radiation source. Radiation may be projected from multiple angles with beams that converge at the target site of ablation.

In the context of various embodiments described herein, localizing a vascular device, such as an energy guide apparatus or an IVUS transducer, is intended to refer to localization of a component or feature of the vascular device. In some embodiments, localization of an energy guide apparatus or and IVUS transducer involves localizing a specific component of the energy guide apparatus or IVUS transducer with high precision. Suitable components or features include those that can be readily detected by an external system and allow for precise measuring of the Cartesian coordinates and orientation angle of the component or feature. Two representative examples of suitable components or features are radiopaque marker(s) and a rotating magnet of an IVUS micro-motor.

By knowing the location of the component or feature of the vascular device, the spatial relationship between the component or feature and the exterior surfaces of a housing or shaft wall that encloses the component or feature can be precisely measured. As such, localization of the component or feature can account for such distances when determining the spacing between the localized component or feature and the inner wall of the renal artery, for example.

According to various embodiments, a distal end of a catheter includes a rotating magnet, a radiopaque component such as a Pt-Ir stator, and an IVUS transducer. Localization of one or more of the IVUS beam source, the rotating magnet, or the radiopaque element can be used to guide a beam of energy from outside the patient to target ablation sites on the renal nerves adjacent the renal artery. Energy sources can include high-intensity focused ultrasound, x-ray, or gamma-ray radiation.

In various embodiments, an ultrasound beam generated at the distal end of a catheter positioned within a renal artery can be received by an external array of ultrasound transducers to locate target ablation sites around the renal artery outside artery wall. The magnetic field of the rotating magnet may be sensed by external magnetic sensors to precisely determine to Cartesian coordinates and orientation angle of the magnet, and help target the ablation. IVUS images may be obtained before, during, and after the ablation to assess the extent and location of the ablation.

According to embodiments that utilize HIFU ablation, an external HIFU array may project beams of ultrasound energy at a frequency in the range of 1 MHz to 5 MHz. In simplified embodiments, the IVUS transducer can generate an ultrasound beam with the same frequency as the external HIFU array. In this case, the HIFU array elements can receive the energy from the IVUS transducer and compute its location relative the HIFU array. In more complex embodiments, either or both of the HIFU array or the IVUS catheter may contain multiple transducers that project beams for ablation or imaging at multiple frequencies.

In some embodiments, an external HIFU array is first operated in a low-intensity imaging mode to create an image of the IVUS catheter to help target the ablation. The magnetic localization may be combined with the external array data to more precisely target ablation sites. The external HIFU array can then operated in the high intensity HIFU mode to ablate target tissue. Meanwhile, the IVUS catheter may be generating images of the tissues surrounding renal artery to detect and assess ablated tissue. The IVUS image may be used to guide the location and intensity of the external beams. In these embodiments, the HIFU transducer elements may operate at a frequency of 1 MHz while the IVUS transducer may operate at 40 MHz.

A benefit gained by generating an ultrasound beam in the IVUS catheter that is sensed by the external HIFU array is that attenuation by tissue occurs on a single pass of the beam through the tissue. By contrast, echo imaging suffers attenuation going into and coming back out of tissue. Another benefit can be gained by using the external HIFU array for imaging and using the internal ultrasound transducer (e.g., an IVUS) to generate the beam of ultrasound energy may yield resolution high enough to identify nerve bundles. Using this approach would allow renal nerves that lie farther from the lumen of the renal artery to be targeted. For example, renal nerves have been found lying up to 7 mm away from a renal artery, especially in the direction of the renal vein. When targeting perivascular renal nerves lying relatively far from the renal arteries, it is important to image neighboring organ tissue, such as the colon or renal vein, to avoid abating such tissues.

Multiple methodologies exist for locating the tip of a catheter placed within the body. One methodology involves sensing the magnetic field of a rotating magnet at the catheter tip with an array of external magnetic sensors. Another methodology involves using an external array of ultrasound transducers in a low-intensity imaging mode to generate an image of the catheter and surrounding tissues. In this mode, the image of the catheter tip may be enhanced by inflating a tip balloon with ultrasound contrast media or constructing the distal catheter with ultrasound reflective materials. A further methodology involves projecting a rotating beam of ultrasound energy from the catheter tip that is sensed by the external array used to locate the catheter tip. Another methodology involves generating a CT scan of the region of the renal artery to image one or more radiopaque elements in the catheter tip. This image may be enhanced by injecting x-ray contrast media into the artery and/or into a balloon at the catheter tip.

Other localization methodologies may be used in accordance with other embodiments including, for example, generating magnetic fields in the region of the catheter tip from an array of external currents, and sensing these magnetic fields using magnetic sensors in the catheter tip for localization. In other embodiments, high frequency electrical currents may be conducted into the patient from strategically located leads placed on the patient's skin. Localization can be accomplished by sensing these currents with exposed electrodes at one or more sites proximate the catheter tip.

A variety of methodologies may be used for co-registering external equipment and images. Representative examples include optical, RF or radio, ultrasound and magnetic field means to send and sense signals between catheters in the body and external equipment and between external equipments. Co-registration between imaging modalities may be enhanced by attaching markers to the patient that show up in the multiple images. In some configurations, the markers are anatomical features of the patient.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

Figure 2A:
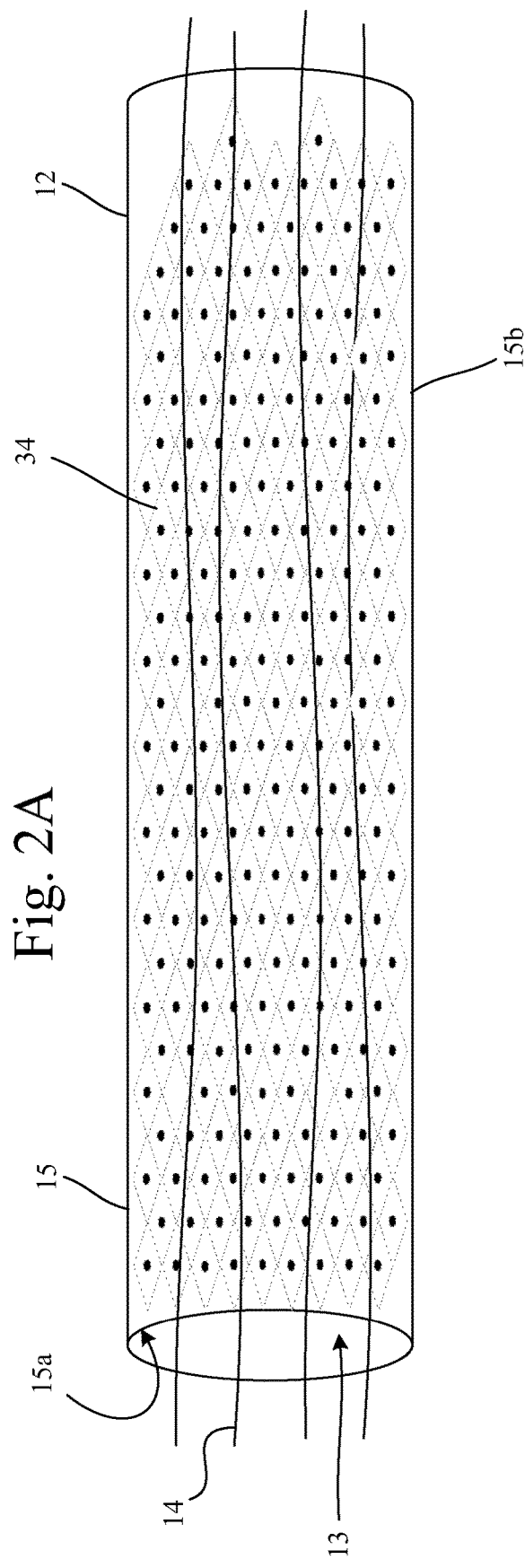
FIGS. 2A and 2B illustrate sympathetic innervation of the renal artery.
Figure 2B:
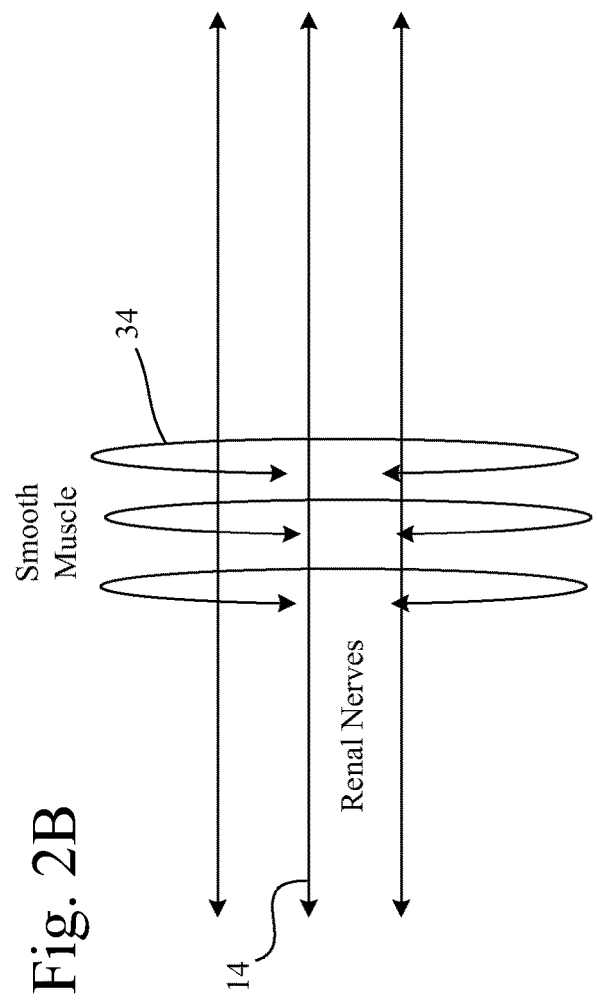

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
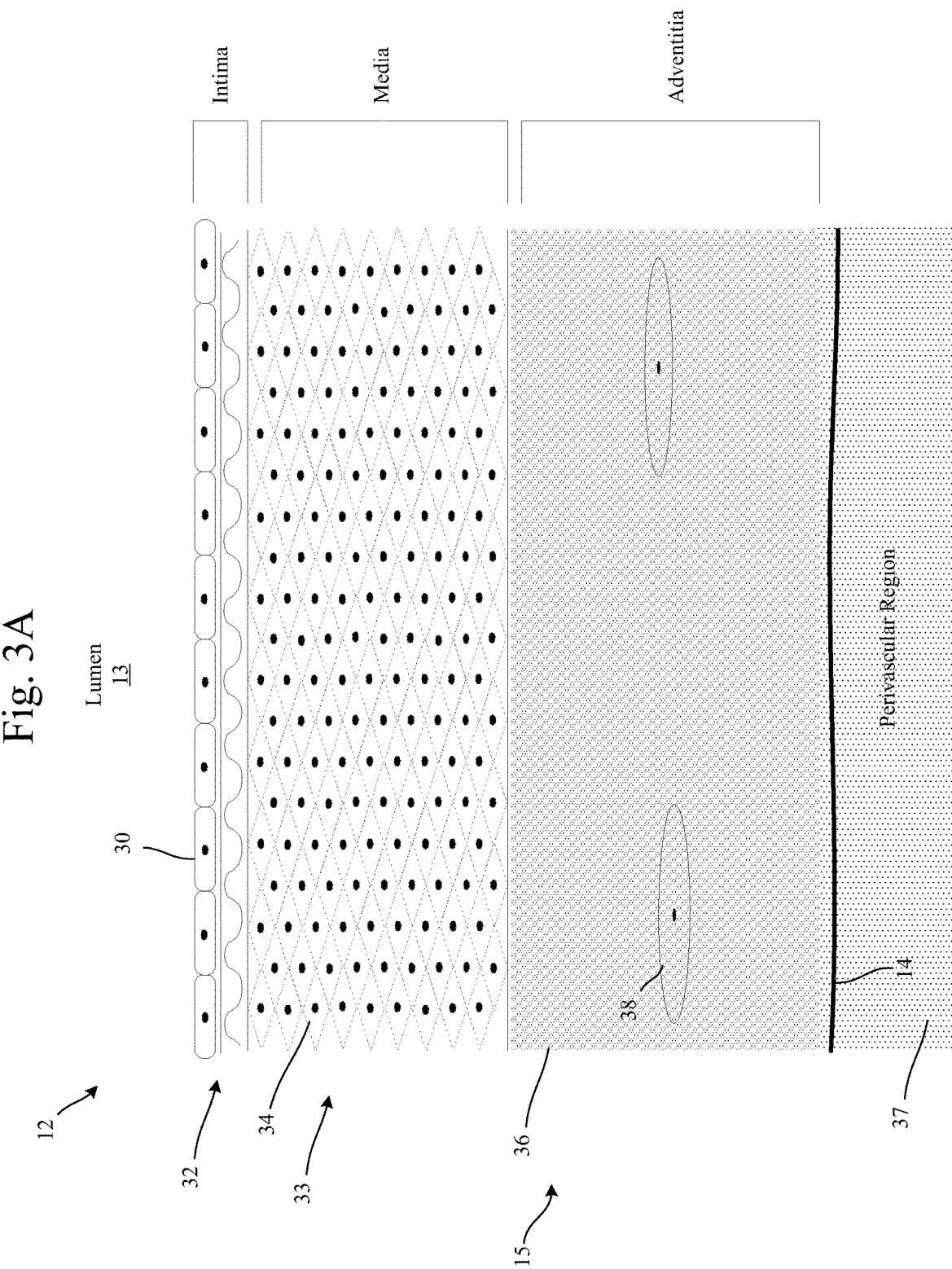
FIG. 3A illustrates various tissue layers of the wall of the renal artery.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3B:
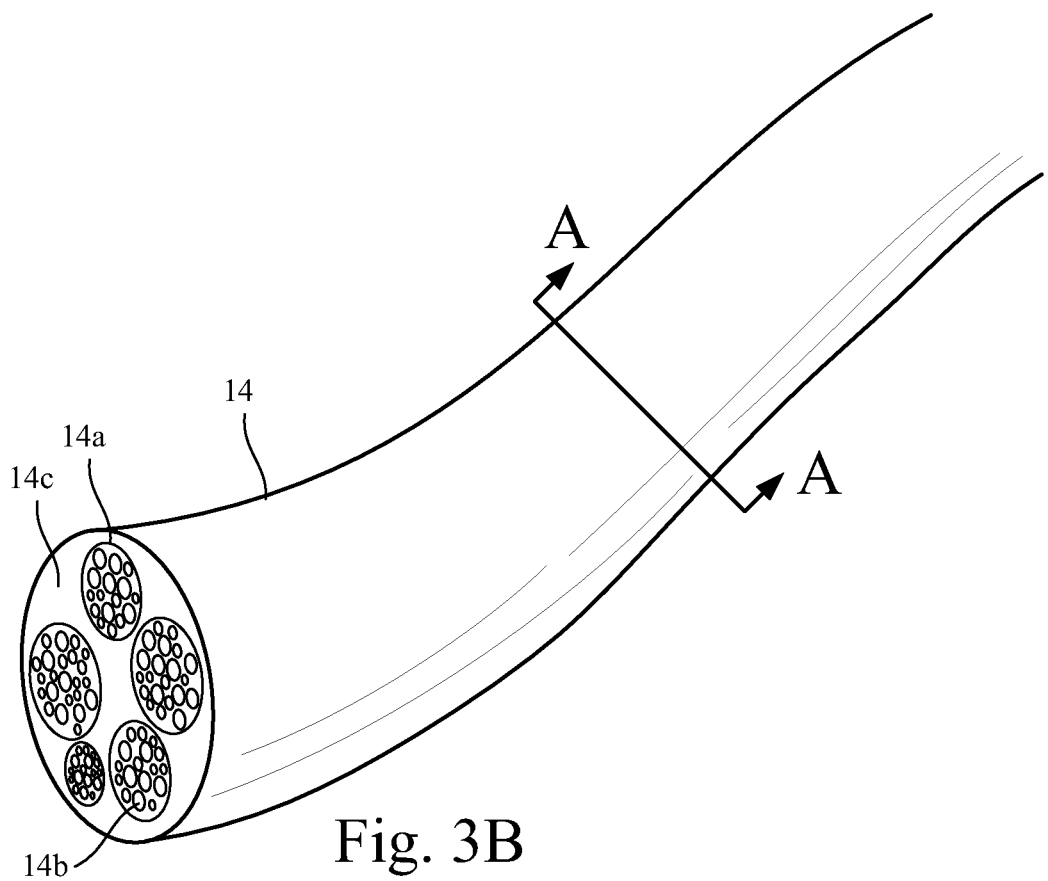
FIGS. 3B and 3C illustrate a portion of a renal nerve.
Figure 3C:
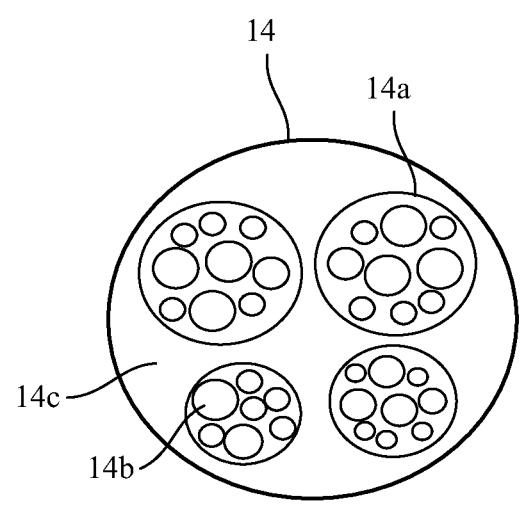

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In preferred embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may be implemented to deliver a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may be implemented to deliver a denervation therapy that interrupts conduction of nerve impulses along the renal nerve fibers 14b by imparting damage to the renal nerve fibers 14b consistent with neruapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a treatment apparatus according to embodiments of the disclosure.

A treatment apparatus may be implemented to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b is preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

A treatment apparatus may be implemented to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Figure 4:
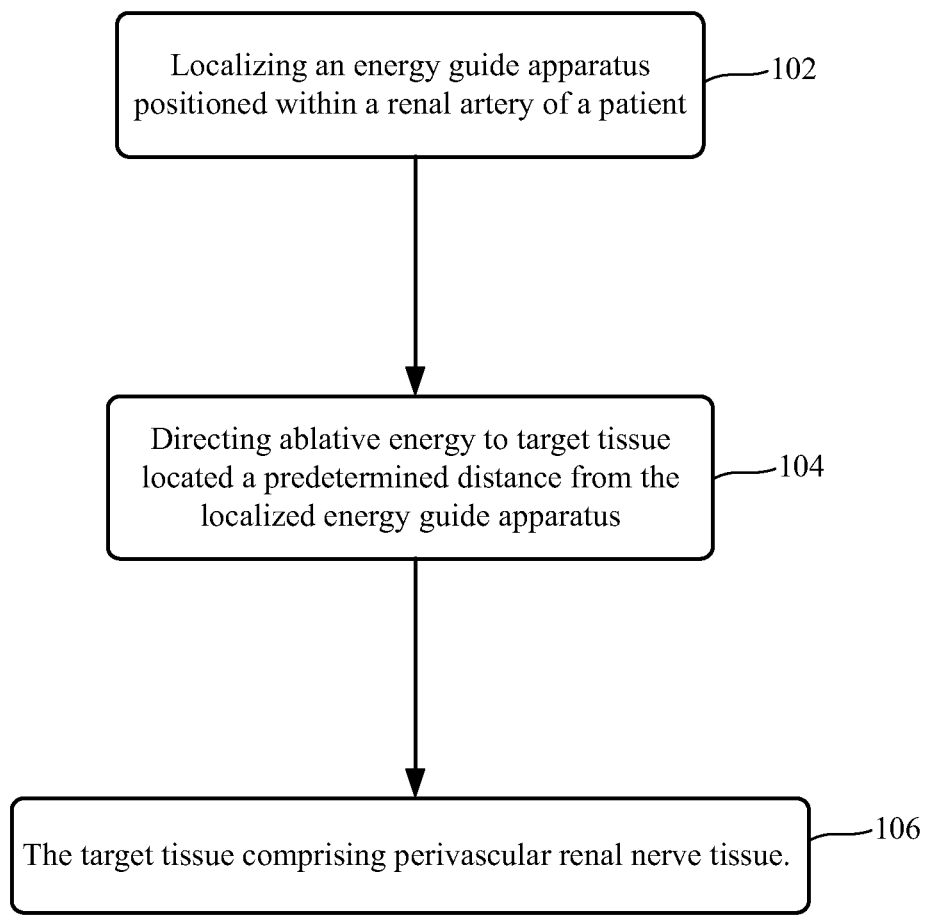
FIG. 4 is a flow chart illustrating various processes of a method for guiding externally generated ablative energy to target tissue of the body in accordance with various embodiments.

In accordance with various embodiments, and as illustrated in FIG. 4, methods of the disclosure involve localizing 102 an energy guide apparatus positioned within a renal artery of a patient. Methods of the disclosure involve directing 104 ablative energy to target tissue located a predetermined distance from the localized energy guide apparatus. The target tissue includes perivascular renal nerve tissue 106 adjacent the renal artery.

Figure 5:
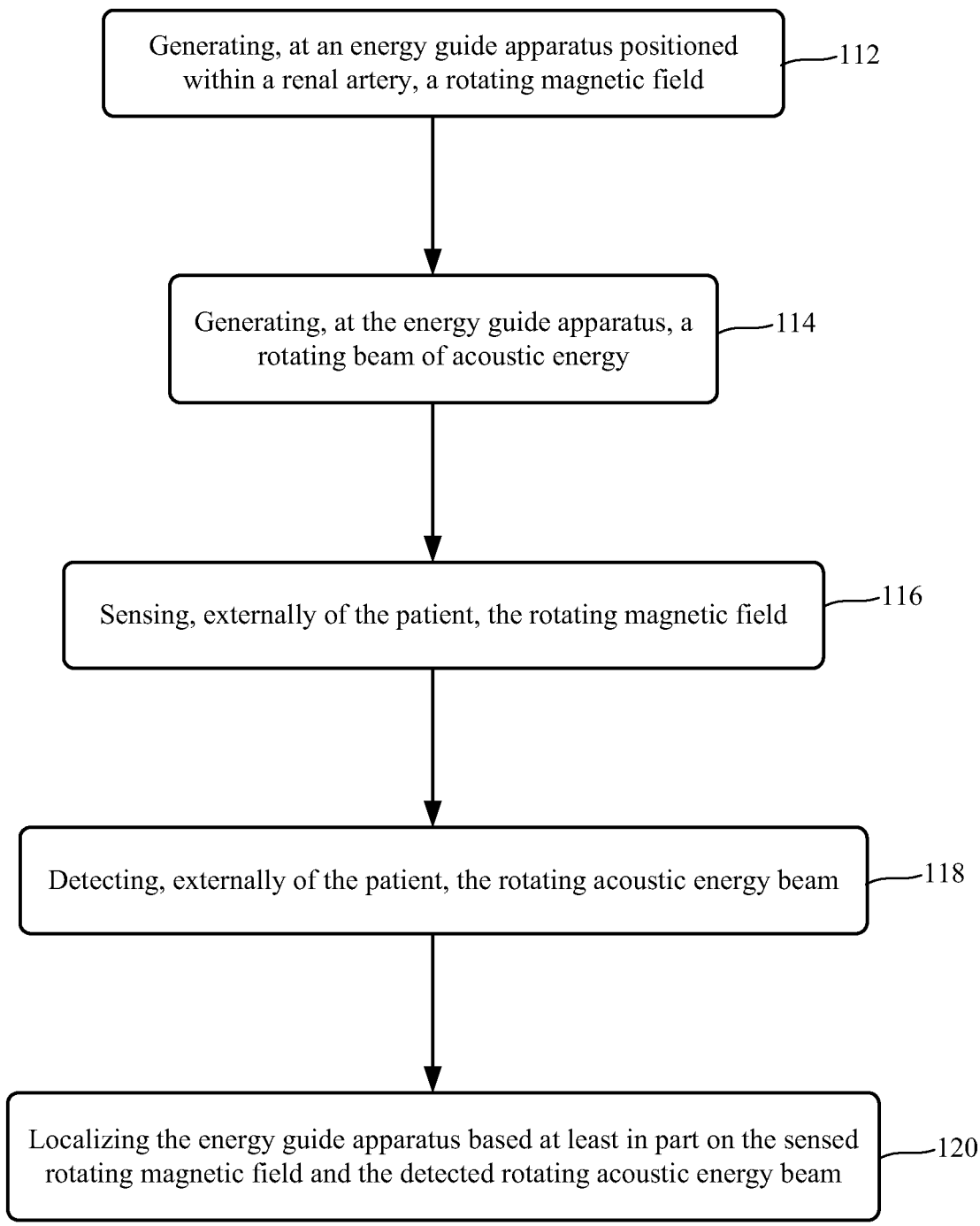
FIG. 5 is a flow chart illustrating various processes of a method for guiding externally generated ablative energy to target tissue of the body based on a rotating magnetic field and a rotating beam of acoustic energy generated from within a patient's renal artery in accordance with various embodiments.

As shown in FIG. 5, various method embodiments involve generating, at an energy guide apparatus positioned within a renal artery, a rotating magnetic field 112 and a rotating beam of acoustic energy 114. Methods also involve externally sensing 116 the rotating magnetic field and detecting 118 the rotating acoustic energy beam. Methods further involve localizing 120 the energy guide apparatus based at least in part on the sensed rotating magnetic field and the detected rotating acoustic energy beam.

Figure 6:
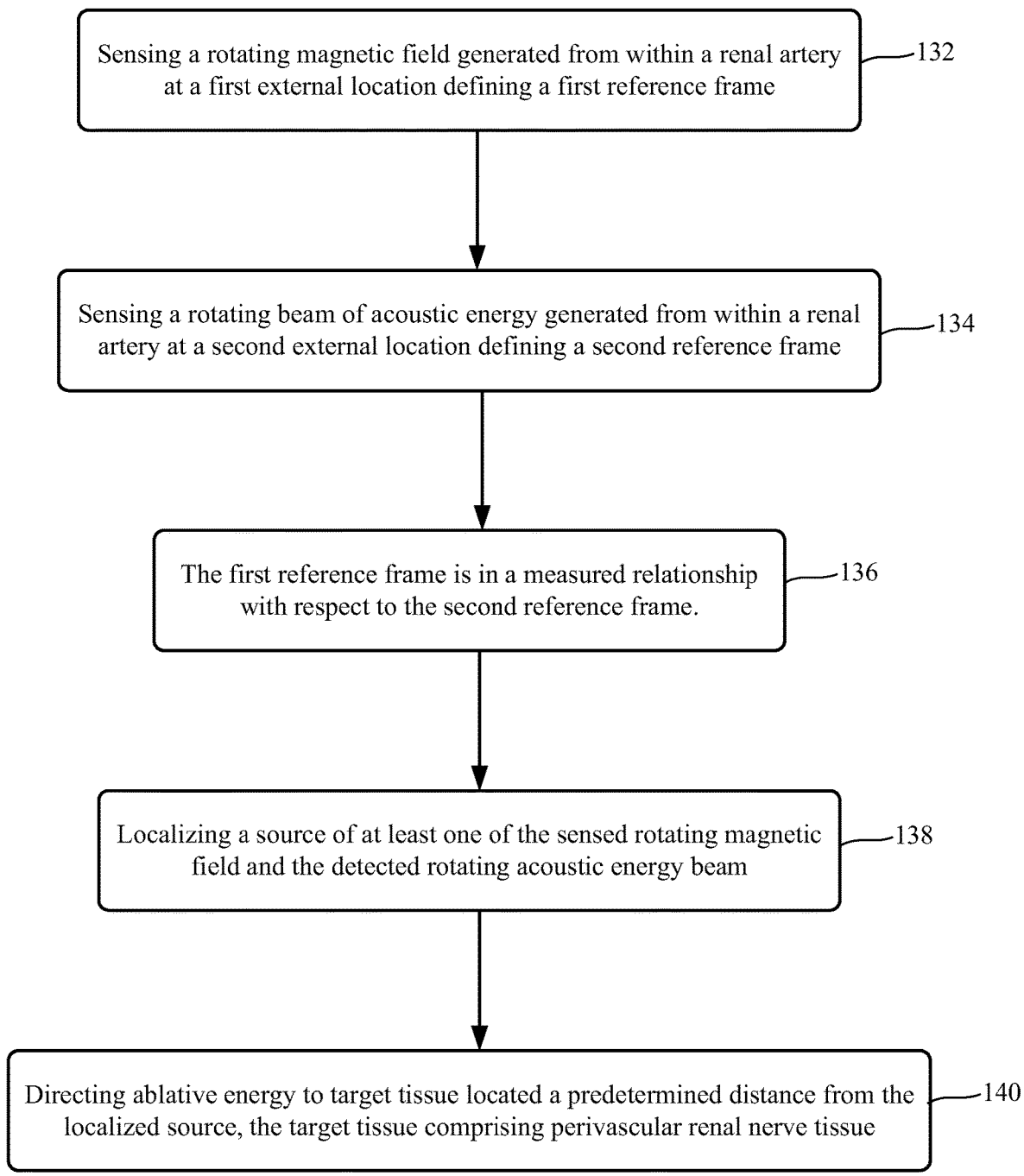
FIG. 6 is a flow chart illustrating various processes of a method for guiding externally generated ablative energy to target tissue of the body based on a rotating magnetic field and a rotating beam of acoustic energy generated from within a patient's renal artery in accordance with various embodiments.

According to other embodiments, and as illustrated in FIG. 6, methods of the disclosure involve sensing 132 a rotating magnetic field generated from within a renal artery at a first external location defining a first reference frame. Methods involve sensing 130 for a rotating beam of acoustic energy generated from within the renal artery at a second external location defining a second reference frame. The first reference frame is in a measured relationship 136 with respect to the second reference frame. Methods also involve localizing 138 a source of at least one of the sensed rotating magnetic field and the detected rotating acoustic energy beam. Methods further involve directing 140 ablative energy to target tissue located a predetermined distance from the localized source, the target tissue including perivascular renal nerve tissue.

Figure 7:
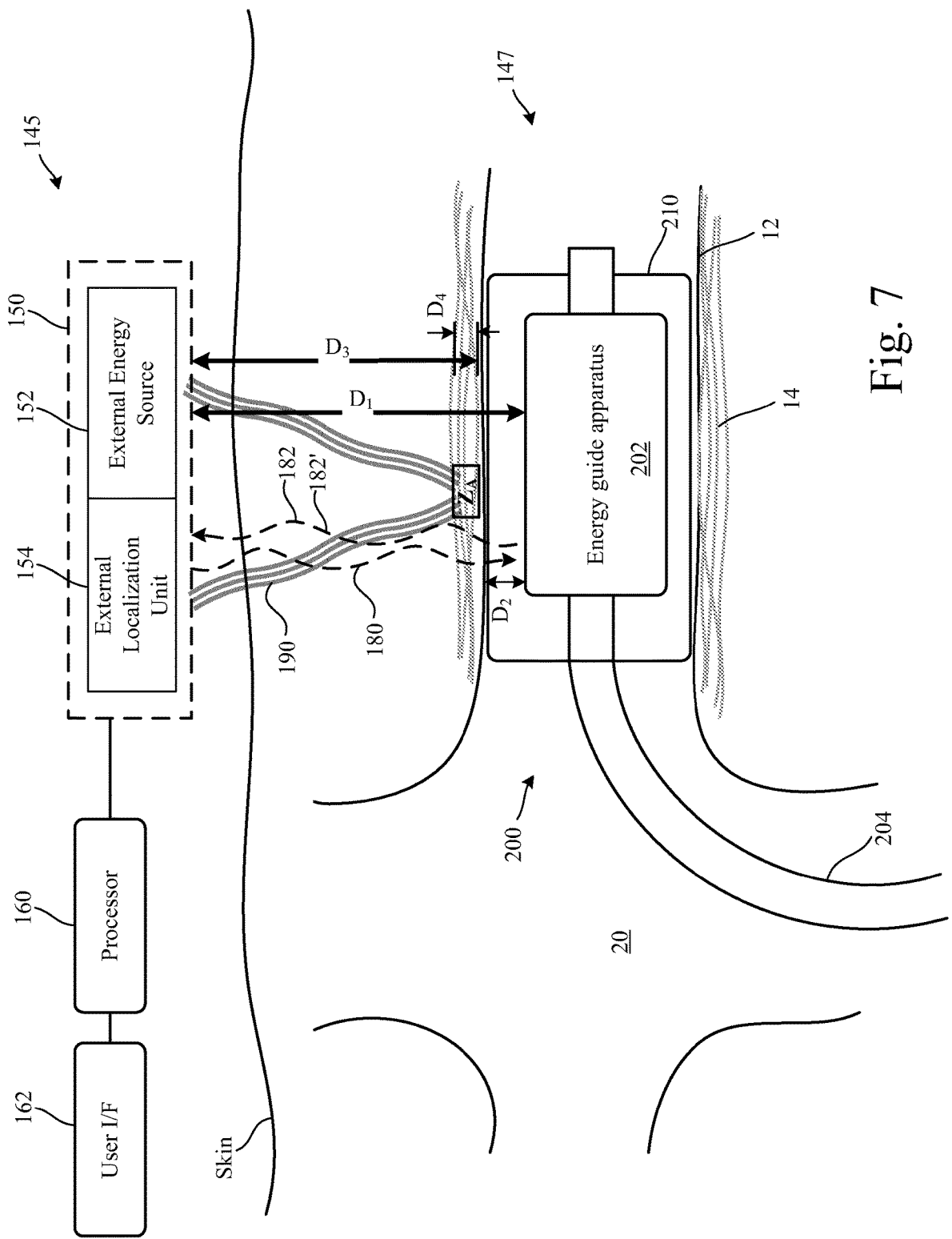
FIG. 7 illustrates an apparatus for guiding externally generated ablative energy to target tissue of the body in accordance with various embodiments.

Turning now to FIG. 7, there is illustrated and apparatus for directing externally generated ablative energy to target tissue within the body in accordance with various embodiments. The apparatus shown in FIG. 7 includes an ex vivo apparatus 145 and an in vivo apparatus 147. The in vivo apparatus 147 includes a catheter 200 which includes a flexible shaft 204 having a proximal end, a distal end, and a length sufficient to access a patient's renal artery 12 relative to a percutaneous access location. The in vivo apparatus 147 also includes an energy guide apparatus 202 provided at the distal end of the shaft 204 and dimension for deployment within the renal artery 12. A support structure 210 is preferably provided at the distal end of the shaft 204 and is transformable between a low-profile introduction configuration and a deployed configuration (e.g., a centering balloon or a centering basket). In some embodiments, the support structure 210 includes a centering basket with four struts, which allows flowing blood to cool the artery wall and the heat producing components (e.g., acoustic transducer) of the energy guide apparatus 202. The support structure 210 serves to center the energy guide apparatus 202 within the renal artery 12 when in the deployed configuration.

The ex vivo apparatus 145 includes an arrangement 150, 160 configured to localize the energy guide apparatus 202 positioned within the renal artery 12. The arrangement 150 includes an external localization unit 154 and an external energy source 152. The external energy source 152 is configured to direct ablative energy to target tissue located a predetermined distance from the localized energy guide apparatus 202 (e.g., a localized component or feature of the energy guide apparatus 202), the target tissue including perivascular renal nerve tissue.

In some embodiments, the external localization unit 154 is configured to generate localization energy 180 that propagates to the energy guide apparatus 202 through the skin and intervening body tissue. In the case of the energy guide apparatus 202 being configured as a passive apparatus, the external localization unit 154 receives a response 182 reflected from, or otherwise responsively produced by, the energy guide apparatus 202. Localization of the energy guide apparatus 202, in this scenario, is performed by the external localization unit 154 and processor 160. According to a representative embodiment employing a passive energy guide apparatus 202, the external localization unit 154 can include a CT scanner and the passive energy guide apparatus 202 may include one or more radiopaque markers.

In other embodiments, the energy guide apparatus 202 is configured as an active apparatus that generates a beacon 182 which can be detected by the external localization unit 154. The energy guide apparatus 202 may be configured to generate a beacon 182 or a multiplicity of beacons 182, 182'. In some embodiments, a single acoustic energy beacon 182 may be generated by the energy guide apparatus 202, which is received by an array of acoustic transducers provided at the external localization unit 154. The energy guide apparatus 202 may be configured to generate an acoustic energy beacon 182 and a magnetic field which also serves as an energy beacon 182'. In this scenario, the external localization unit 154 includes an array of magnetic fields sensors and an array of acoustic transducers for detecting the acoustic and magnetic field energy beacons 182 and 182', respectively. It is understood that various combinations of active and passive components can be incorporated in one or both of the ex vivo and in vivo apparatuses 145 and 147.

The external localization unit 154 cooperates with the processor 160 to determine the precise position and orientation of the energy guide apparatus 202 positioned within the renal artery 12. For purposes of simplicity of explanation, the localization of the energy guide apparatus 202 shown in FIG. 7, which typically involves determining three-dimensional Cartesian coordinates and an orientation angle, is depicted as a distance, $D_1$, between the external localization unit 154 and the energy guide apparatus 202. A distance, $D_2$, between the energy guide apparatus 202 and an inner wall surface of the renal artery 12, is measured either by the apparatus of FIG. 7 (e.g., low-intensity ultrasound imaging) or a separate procedure such as quantitative angiography of the renal artery 12. The difference between the two distances $D_1$ and $D_2$ provides a precise location of the renal artery's inner wall relative to the external localization unit 154. The difference between these two distances is offset by a small distance to avoid ablating the renal artery wall.

The offset can be selected based on the anatomy of a particular patient (e.g., by imaging a region from 0 mm to about 1 mm away from the renal artery lumen wall) or on patient population data. As discussed previously, human renal nerves are typically found lying within 3.5 mm of a renal artery lumen wall, but have been found lying as close as about 0.5 mm and as far out as about 7 mm from the renal artery lumen wall. As such, an offset of about 0.5 mm would provide a high likelihood that renal nerves closest to a renal artery will be ablated, although an offset between about 1 to 2 mm may be acceptable in many cases. A minimum safe offset is preferably one that ensures that the artery wall is not subjected to ablative energy 190 produced by the external energy source 152.

In some embodiments, an additional offset, D4, may be included to define a zone of ablation, shown as $Z_A$, which, in actuality, is a three-dimensional volume. A maximum additional offset, D4, may be based on the maximum depth (a distance from the renal artery lumen wall projecting normal from the wall into adjacent perivascular space) of the ablation zone $Z_A$, not exceeding about 7 mm from the renal artery lumen wall. Imaging perivascular space within 7 mm from the renal artery lumen wall can be useful for establishing the additional offset, D4.

The external energy source 152 directs high-intensity energy or radiation 192 to the target perivascular renal nerves 14. The external energy source 152 typically produces spot lesions, and a multiplicity of spot lesions may be produced within an ablation zone, $Z_A$. Ablation is preferably performed at points around the periphery of the renal artery 12. The external energy source 152 may need to be moved to two or more positions relative to the patient's renal artery 12 to complete a circumferential ablation. As discussed previously, the energy guide apparatus 202 may include an ultrasound transducer (alone or in conjunction with an external imaging array) that can be used to image adjacent tissue to assess the extent and location of the ablation. Images, data, and other information about the ablation procedure can be displayed on a user interface 162, which is coupled to the processor 160.

Figure 8:
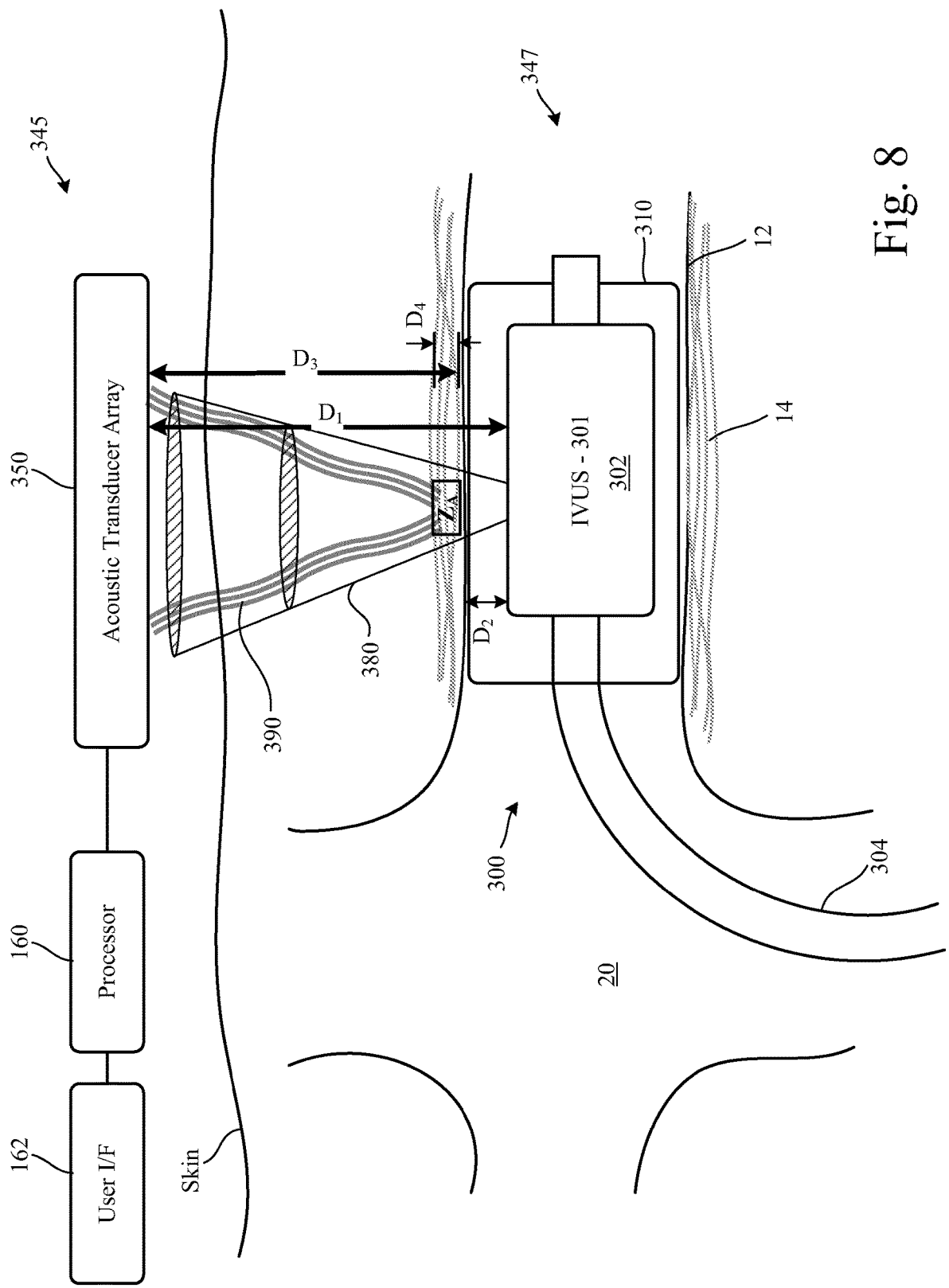
FIG. 8 illustrates an apparatus for guiding externally generated, high-intensity ablative acoustic energy to target tissue of the body in accordance with various embodiments.

FIG. 8 illustrates an apparatus for directing externally generated high-intensity acoustic energy to target tissue of the body, such as perivascular renal nerves adjacent a patient's renal artery. In the embodiment shown in FIG. 8, an in vivo apparatus 347 includes a catheter 300 comprising a flexible shaft 304 having a length sufficient to extend between a patient's renal artery 12 and a percutaneous access location. An energy guide apparatus 302 is provided at a distal end of the shaft 304. The distal end of the shaft 304 further includes a support structure 310 which is transformable between a low-profile introduction configuration and a deployed configuration. As previously discussed, the support structure 310 serves to center the energy guide apparatus 302 within the lumen of the renal artery 12.

The energy guide apparatus 302 includes an intravascular ultrasound device 301 configured to generate a rotating beam of acoustic energy. A micro-motor of the IVUS 301 causes a mirror (acoustic reflector) to rotate at a precisely known target frequency. A stationary ultrasound transducer emits ultrasound energy which is reflected by the rotating mirror in a direction perpendicular to a longitudinal axis of the IVUS housing/shaft's distal end. According to this configuration, the IVUS 301 generates a conical beam of acoustic energy that rotates at the precisely known target frequency. This rotating acoustic energy beam can be detected externally of the patient.

In the embodiment illustrated in FIG. 8, the ex vivo apparatus 345 includes an acoustic transducer array 350 which is configured to detect the rotating beam of acoustic energy emitted by the IVUS 301. The acoustic transducers of the array 350 may operate at the same frequency as that/those of the IVUS 301, allowing for identification and synchronous detection of the IVUS 301 (e.g., the rotating magnet of the IVUS 301). The processor 160 cooperates with the acoustic transducer array 350 to determine the position and orientation of the IVUS 301, and to compute the distance $D_1$, between the array 350 and the IVUS 301, and the distance $D_2$, between the inner wall of the renal artery 12 and the IVUS 301. Based on these distances, which in actuality are Cartesian coordinates and an orientation angle, the distance $D_3$ between the array 350 and target perivascular renal nerve tissue 14 is computed. As discussed previously, an offset between about 0.5 and 2 or 3 mm is included to avoid ablating the wall of the renal artery 12. An additional offset, shown as the distance $D_4$, can be included to define a region of ablation, $Z_4$. According to some embodiments, the acoustic transducer array 350 is configured to operate as an acoustic detector array for detecting the rotating beam of acoustic energy emitted by the IVUS 301. The acoustic transducer array 350 is also configured to operate as a high-intensity acoustic ablation array that directs high-intensity acoustic energy to the target tissue for ablating the target tissue.

Figure 9:
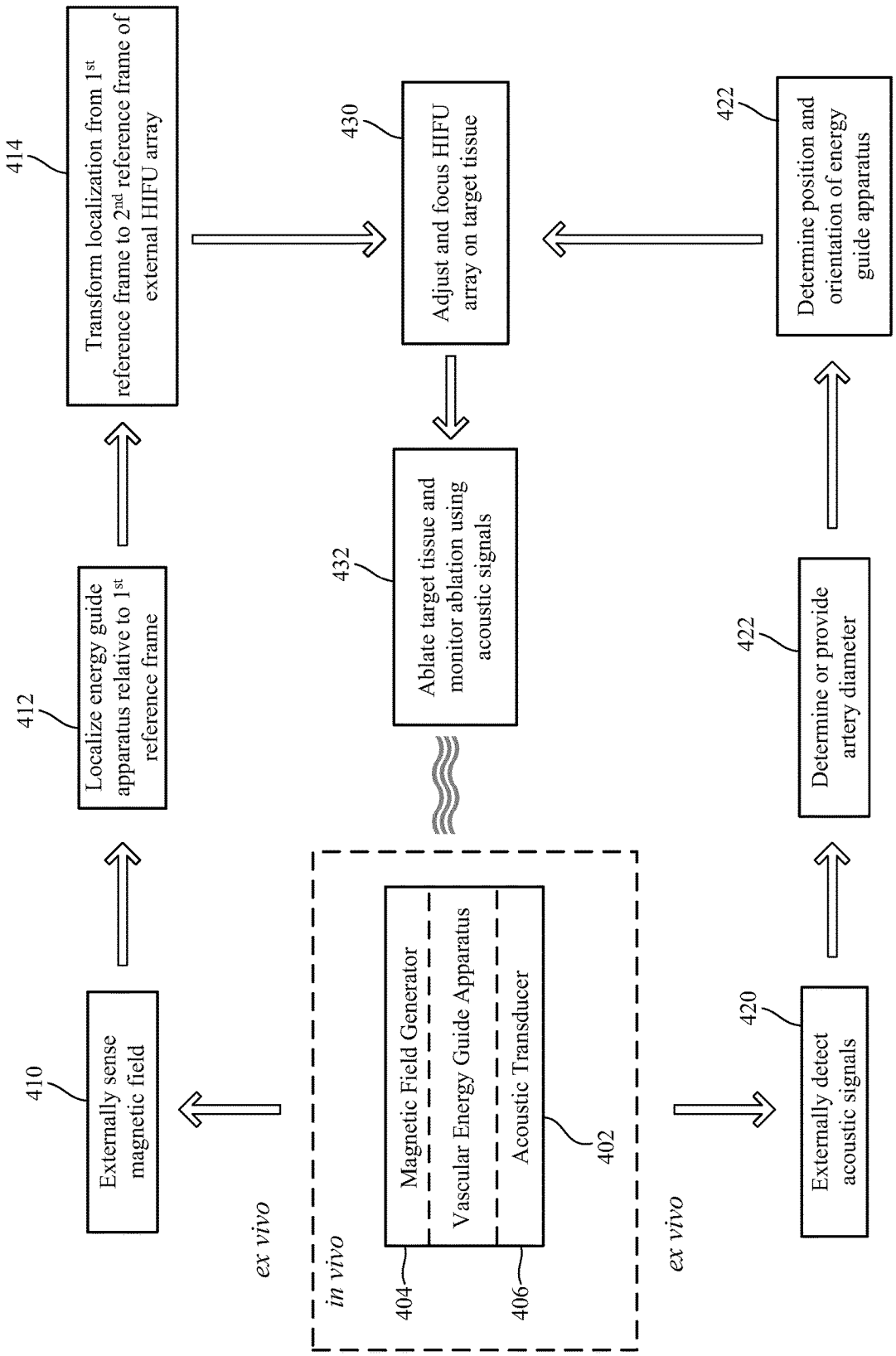
FIG. 9 illustrates an apparatus for guiding externally generated ablative energy to target tissue of the body in accordance with various embodiments.
Figure 10:
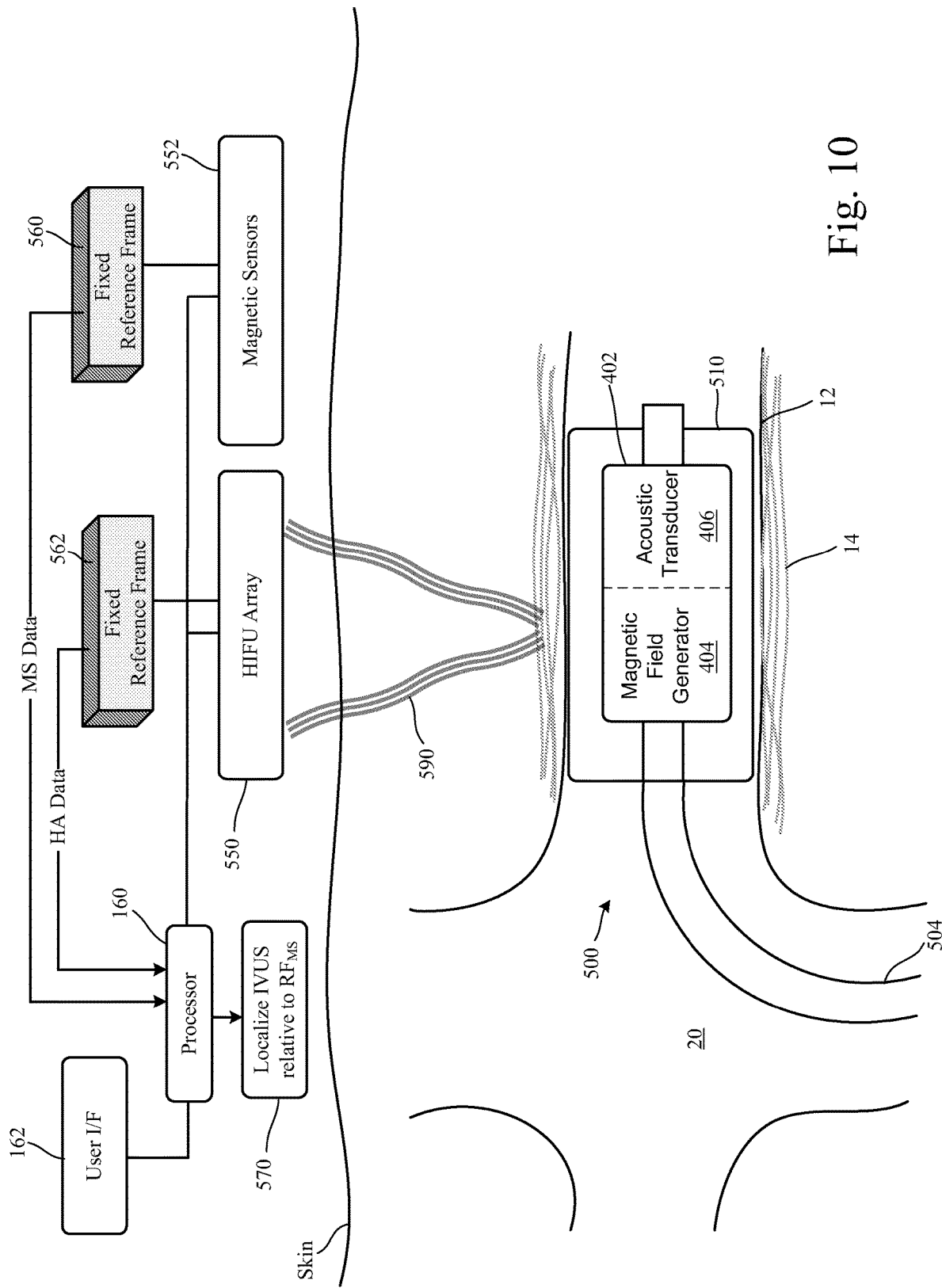
FIG. 10 illustrates an apparatus for guiding externally generated ablative ultrasound energy to target tissue of the body based on a rotating magnetic field and a rotating beam of acoustic energy generated from within a patient's renal artery in accordance with various embodiments.

Referring now to FIGS. 9 and 10, there is illustrated a flow block diagram (FIG. 9) and a system block diagram (FIG. 10) illustrating various apparatuses and processes for guiding externally generated high-intensity energy to target tissue of the body. In the embodiment shown in FIGS. 9 and 10, an energy guide apparatus 402 is provided at a distal end of the shaft 504 of a catheter 500. The energy guide apparatus 402 includes an acoustic transducer 406 and a magnetic field generator 404. The acoustic transducer 406 is preferably configured to generate a rotating beam of acoustic energy at a target frequency which can be externally detected 420, such as by an external HIFU array 550. The acoustic transducer 406 may be configured as an IVUS, such as the IVUS 700 shown in FIG. 12. The externally detected acoustic signals 420 may be used to determine the diameter of the renal artery 12. In some embodiments, optical magnetometers can be used to facilitate measuring of the renal artery's diameter. The artery diameter measurement can be used to determine a distance between the energy guide apparatus 402 and inner wall of the renal artery 12. The externally detected acoustic signals 420 may also be used to determine the position and orientation of the energy guide apparatus 402 for purposes of enhancing localization accuracy (shown as HA data communicated to the processor 160).

The magnetic field generator 404 of the energy guide apparatus 402 is configured to generate a rotating magnetic field which can be sensed externally 410, such as by an array of magnetic sensors 552 defining a first reference frame 560. Suitable magnetic sensors for the array 552 include, for example, magnetic induction (wire wound around a magnetic core) sensors, flux gate magnetometers, saturable core magnetometers, Hall effect sensors, Superconducting Quantum Interference Device ("SQUID") magnetometers, and giant magnetoresistance ("GMR") sensors. The externally sensed magnetic field 410 is communicated as magnetic sensor data (MS data) to the processor 160. The processor 160 uses the magnetic sensor data to localize 412/570 the energy guide apparatus 402 relative to the first reference frame 560. The processor 160 may also use localization data produced by the HIFU array 550 in response to detecting the rotating beam of acoustic energy produced by the acoustic transducer 406 to enhance the accuracy of localization measurements as discussed previously.

The external HIFU array 550 is configured to produce high-intensity ultrasound energy that can be focused at target tissue of the body. In order to positionally synchronize the first reference frame 560 of the magnetic sensor array 552 with a second reference frame 562 of the HIFU array 550, one approach involves transforming the Cartesian coordinates and orientation angle of the energy guide apparatus localized with respect to the first reference frame to corresponding Cartesian coordinates and orientation angle of the second reference frame. Using the transformed localization of the energy guide apparatus 412, 414 and (optionally) the position and orientation of the energy guide apparatus determined 422 using the detected acoustic signals, the external HIFU array 550 is adjusted to focus high-intensity ultrasound energy at the target tissue. The target tissue is ablated, and the ablated tissue and surrounding tissue may be monitored using the acoustic signals 432 generated by the acoustic transducer 406 and/or the HIFU array 562 operating in a low-intensity imaging mode.

According to other embodiments, and with continued reference to FIG. 9, the energy guide apparatus 402 can be positioned and operated at a location outside of the renal artery, such as from within a nearby organ or other anatomical structure. Various organs and structures of the body near the renal arteries can be suitable sites for guiding externally generated ablative energy to perivascular renal nerves. Suitable organs and structures include the patient's renal colon (e.g., transverse colon) and a renal vein or other blood vessel in proximity to the renal artery, such as the hepatic portal vein. Access to such alternative sites within the body may be gained preferably via a minimally-invasive body pathway beginning at a natural orifice (e.g., mouth, anus, urethra). For some patients, a more invasive percutaneous access procedure may be required. Additional details concerning embodiments that involve positioning and operating an energy guide apparatus from a location outside of the renal arteries are provided toward the end of the detailed description.

Figure 11:
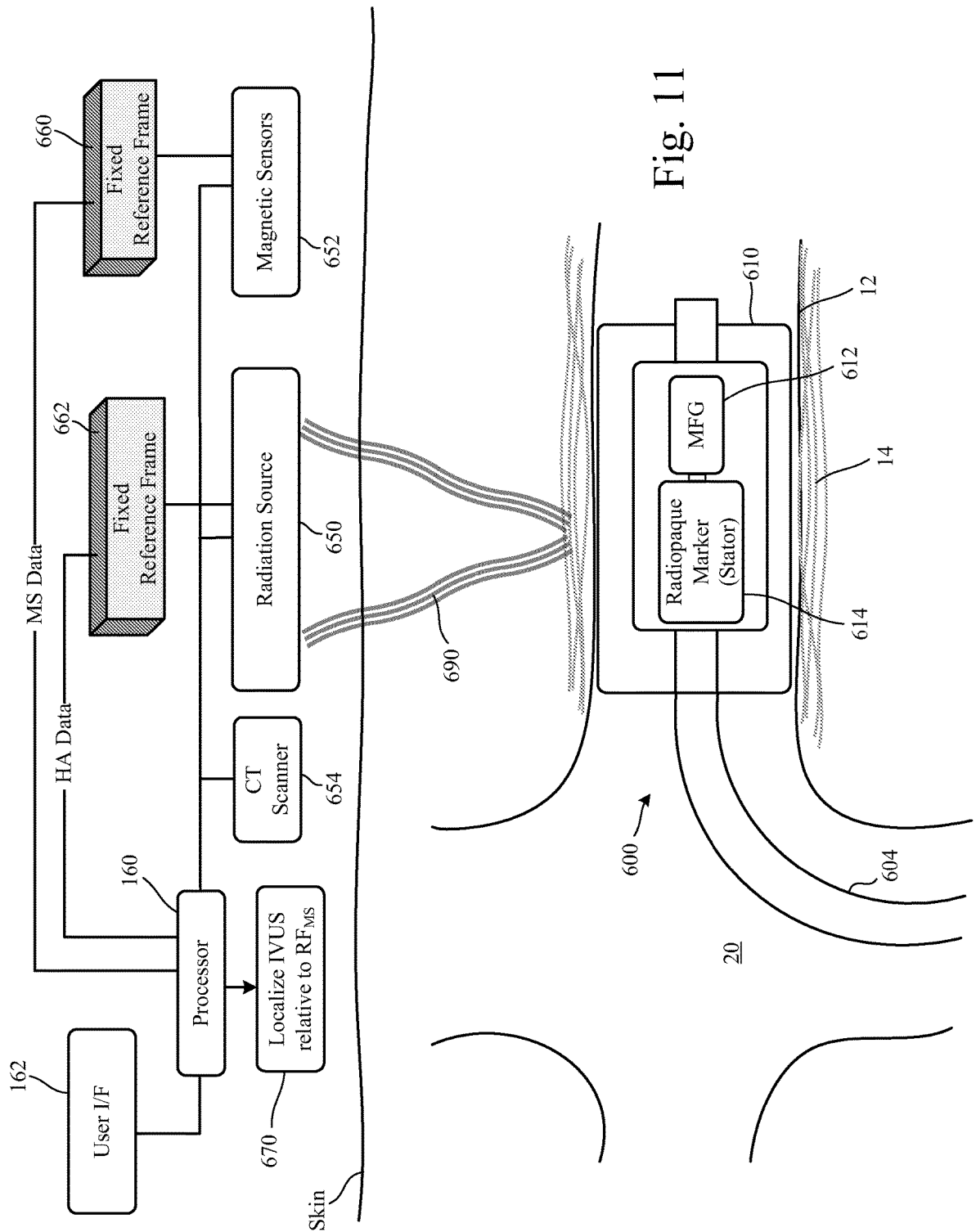
FIG. 11 illustrates an apparatus for guiding externally generated ablative radiation to target tissue of the body based on a rotating magnetic field generated from within a patient's renal artery and a radiopaque marker positioned within the patient's renal artery in accordance with various embodiments.

In the embodiment illustrated in FIG. 11, the external energy source is preferably a radiation source 650, such as an x-ray radiation source or a gamma-ray radiation source. According to the embodiment shown in FIG. 11, the energy guide apparatus 602 includes a magnetic field generator (MFG) 612 configured to generate a rotating magnetic field and at least one radiopaque marker 614. In this embodiment, the MFG 612 need not be a component of an IVUS, but may instead be a stand-alone device. In other embodiments, the MFG 612 can be a component of an IVUS. The radiopaque marker 614 is preferably situated on a component structure that is not rotating, and is readily detectable by an external CT scanner 654. For example, the MFG 612 may include a Pt-Ir stator.

According to some embodiments, the CT scanner 654 is used to localize the energy guide apparatus 602. In other embodiments, the rotating magnetic field sensed by the array of magnetic sensors 652 is used to provide real-time localization of the energy guide apparatus 602, in addition to localization provided by the scan produced by the CT scanner 654. The CT scan may be displayed on the user interface 162 and co-registered with the reference frame 660 of the magnetic localization system 652 and the reference frame 662 of the external radiation source 650. Upon completion of energy guide apparatus localization, radiation is emitted from the radiation source 650 and directed to the computed target tissue. The radiation may be emitted from multiple angles with beams that converge on the target site of the ablation (e.g., perivascular renal nerves 14).

Figure 12:
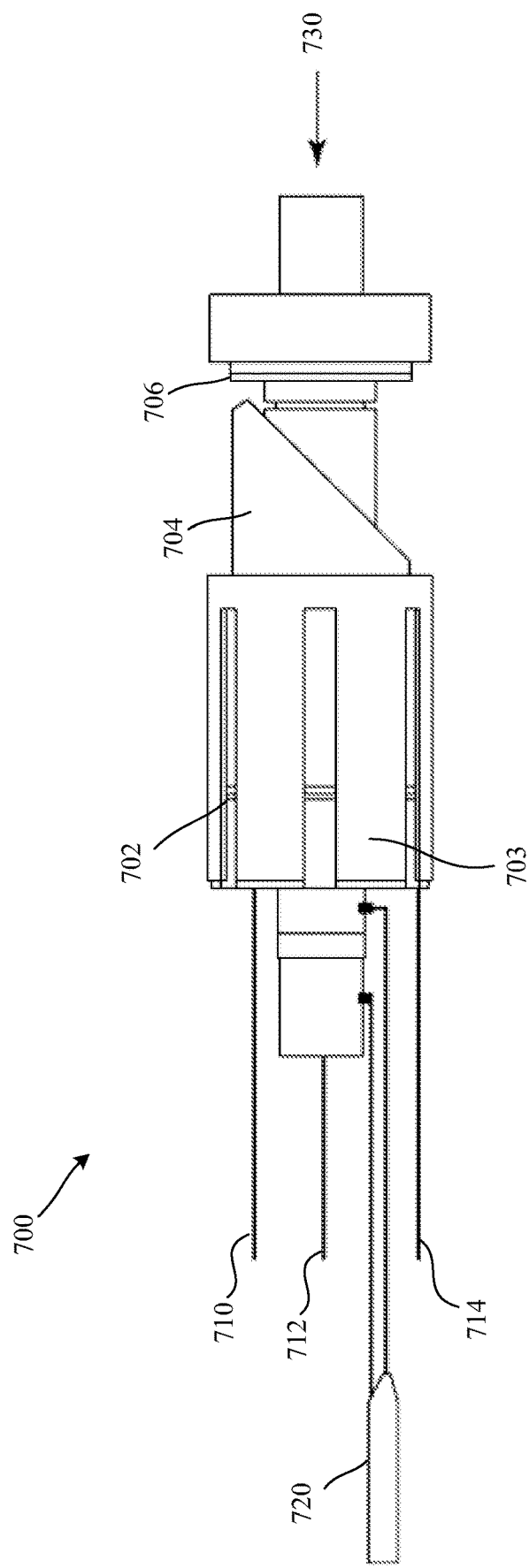
FIG. 12 illustrates an intravascular ultrasound device useful in an apparatus for guiding externally generated ablative energy to target tissue of the body.

FIG. 12 illustrates an embodiment of an IVUS 700 in accordance with various embodiments. The IVUS 700 shown in FIG. 12 is well-suited for incorporation in energy guide apparatuses according to previously described embodiments. FIG. 12 illustrates a micro-motor driven IVUS imaging core. A micro-motor 702 comprises a slotted tube stator 703 into which three phase current, for example, is injected to create a rotating magnetic field within the stator 703. The rotating magnetic field rotates a magnet and an attached mirror 704 to reflect a beam of ultrasound energy from the transducer 706 into tissue in the plane perpendicular to the longitudinal axis of the device 700.

The magnet of the IVUS 700 is driven to rotate at a precisely known target frequency by a magnetic field generated by, for example, the stator windings (e.g., air core) of the slotted tube stator 703. According to some embodiments, while the externally sensed magnetic field is a combination of those created by the stator windings and the rotating magnet, the magnetic field of the rotating magnet is orders of magnitude larger than the magnetic field of the stator windings. The magnetic field rotates at the precisely known frequency of the stator drive currents supplied to current lines 710, 712, and 714. The current lines extend along the length of a flexible shaft that supports the IVUS 700 to a proximal connection interface.

The ultrasound transducer 706 can include one or more ultrasound transducer elements. The ultrasound transducer 706 is positioned to remain stationary relative to a rotatably mounted mirror 704, which serves as an acoustic reflector. Rotation of the magnet of the micro-motor 702 causes corresponding rotation of the mirror 704 at the target frequency. The ultrasound transducer 706 includes coaxial cable 720 that extends along the length of the IVUS catheter shaft. As previously discussed, the stationary ultrasound transducer 704 emits ultrasound energy which is reflected by the rotating mirror 704 in a direction perpendicular to a longitudinal axis of the IVUS device.

According to the configuration shown in FIG. 12, the IVUS 700 generates a conical beam of acoustic energy that rotates at the target frequency. This rotating acoustic energy beam can be detected externally of the patient. Additionally, the micro-motor components generate a magnetic field which can be externally detected as a magnetic field that rotates at the precisely known frequency of the stator drive currents. In some embodiments, one of the rotating acoustic energy beam and the rotating magnetic field is used by an ex vivo apparatus to localize the IVUS 700 (e.g., the rotating magnet of the micro-motor 702. In other embodiments, both the rotating acoustic energy beam and the rotating magnetic field are used for IVUS localization. According to some embodiments, the IVUS 700 includes a guidewire lumen 730 dimensioned to receive a guidewire to facilitate navigation and deployment of the IVUS 700 in the renal artery. For renal denervation, a centering balloon may cover the imaging core and be inflated to center the imaging core within the renal artery.

A spinning magnet generates a rotating magnetic field at points in the space surrounding the magnet. The strength of the magnetic field may be approximately half of the magnet's magnetization at the surface of the magnet, and decreases with the cube of the distance from the spinning magnet. In at least some embodiments, the external localization system includes an array of magnetic sensors positioned outside the patient that synchronously detects the magnetic field created by the magnet as the magnet rotates. In some embodiments, the currents driving the rotating magnet may be used as a reference to provide high resolution measurements. There are many ways to sense a magnetic field. A coil of wire can sense AC magnetic fields. The sensitivity, or signal-to-noise ratio, of the induction coil increases with the coil volume. Thus, large coils can be more sensitive than relatively smaller coils. If compact, small-volume sensors are desired for a given application, then modem sensors, such as GMR sensors, may increase sensitivity.

The magnetic gradient tensor is measured and inverted using a known algorithm to produce the Cartesian coordinates and orientation of the rotating magnet. According to various representative examples, calculations using commercially available magnetic field sensors show that a location of a magnet may be localized to sub-millimeter accuracy when the rotating magnet has an 0.8 mm diameter and a 5 mm length and an array of magnetic sensors is located up to 0.5 meters from the rotating magnet. The accuracy may be improved using many different techniques including, for example, increasing the size of the rotating magnet, increasing the saturation magnetization of the magnet material, increasing the speed of the rotation of the magnet, increasing the interval over which data are averaged (i.e., reducing the sampling rate), increasing the volume of the sensors, increasing the sensitivity of the sensors, reducing the distance between the rotating magnet and the sensor array, increasing the number of magnetic sensors, improving the relative locations of the sensors in the sensor array, sensing the angular position of the magnet as it rotates and providing this data as a reference for a lock in amplifier whose input is a magnetic field sensor, or the like or combinations thereof.

Many sensor arrays are possible, in addition to a tensor array. A minimum of five independent magnetic field measurements are needed to find the three Cartesian coordinates and two orientation angles of the rotor magnet. More redundant sensor outputs may be combined to improve the measurement accuracy. There are many mathematical approaches to inversion of an array of sensor data. One simplification is to note that during one revolution of the rotor (e.g., 1/500 sec at 500 Hz), the position of the distal end of a catheter upon which a rotating magnet is disposed cannot change appreciably. If many magnetic field data samples are collected in a revolution, the assumption that the Cartesian coordinates are the same for all of these samples, simplifies and linearizes the solution for the components of the magnetic moment vector (orientation angles). This data may be combined to solve for the vector that is perpendicular to all of the moment vectors, namely the vector defining a longitudinal axis of the catheter.

Selected features and functionality of an IVUS suitable for incorporation in energy guide apparatuses and in external localization systems and methods described herein are described in commonly owned, co-pending U.S. patent application Ser. No. 13/225,962 filed Sep. 6, 2011; and U.S. Patent Publication Nos. 20100249604; 20110071400;

20110071401; and 20110144479, each of which is incorporated herein by reference in its respective entirety.

The embodiments disclosed herein are generally described in the context of an energy guide apparatus positioned within a lumen of the renal artery. Alternative embodiments are directed to an energy guide apparatus that can be positioned and operated at a location outside of the renal artery, such as from within a nearby organ or other anatomical structure, as previously discussed. For example, an energy guide apparatus can be positioned within the transverse colon at a first location near the left renal artery to guide externally generated ablative energy to perivascular renal nerves proximate the left renal artery. The energy guide apparatus can be repositioned to a second location within the transverse colon near the right renal artery to guide externally generated ablative energy to perivascular renal nerves proximate the right renal artery. The transverse colon can be as close as about 4 mm from the wall of the renal arteries.

According to a minimally-invasive delivery approach, a catheter supporting an energy guide apparatus can be advanced through the mouth and along an upper gastrointestinal access path to a location proximate the renal arteries. In this delivery scenario, the catheter is advanced through the patient's esophagus, stomach, duodenum, small intestine (jejunum and ileum), ascending colon of the large intestine, and to a proximal location (relative to the direction of catheter advancement) within the transverse colon.

The energy guide apparatus is preferably positioned and/or oriented relative to the patient's left renal artery in a manner best suited for guiding externally generated ablative energy to innervated tissue of the left renal artery. After completion of the ablation (and imaging, if desired) procedure for the left renal artery, the catheter is advanced through the transverse colon to a distal location (relative to the direction of catheter advancement) in proximity to the patient's right renal artery. The energy guide apparatus is preferably positioned and/or oriented relative to the patient's right renal artery in a manner best suited for guiding externally generated ablative energy to innervated tissue of the right renal artery. In an alternative delivery approach, the catheter can be advanced through the rectum, into the descending colon of the large intestine, and to appropriate locations within the transverse colon. It is noted that anatomical variations between patient's may require positioning of the energy guide apparatus at locations of the large intestine other than within the transverse colon, such as at or near a distal portion of the ascending colon or proximal portion of the descending colon, for example.

Other organs and structures of the body near the renal arteries can be appropriate sites for guiding externally generated ablative energy to perivascular renal nerves. Suitable organs and structures include the patient's renal vein or other blood vessel in proximity to the renal artery, such as the hepatic portal vein. In some embodiments, renal nerve access can be achieved using a trans-hepatic route via the inferior vena cava and hepatic vein, similar to a TIPS procedure. In various embodiments, renal nerve access can be achieved using a body pathway that includes the inferior vena cava, hepatic vein, liver, and intraperitoneum. Other renal artery access approaches are contemplated, including those disclosed in commonly owned, co-pending U.S. patent application Ser. No. 13/243,134 filed Sep. 23, 2011, which is incorporated herein by reference.

The embodiments disclosed herein are generally described in the context of ablation of perivascular renal nerves for control of hypertension. It is understood, however, that embodiments of the disclosure have applicability in other contexts, such as performing ablation from within other vessels of the body, including other arteries, veins, and vasculature (e.g., cardiac and urinary vasculature and vessels), and other tissues of the body, including various organs.

What is claimed is:

1. An apparatus, comprising:
   an in vivo apparatus comprising:
      a flexible shaft having a proximal end and a distal end; and
      an energy guide apparatus provided at the distal end of the shaft comprising a magnetic field generator configured to generate a rotating magnetic field and an acoustic transducer configured to generate a rotating acoustic beam;
   an ex vivo apparatus comprising:
      a localizing arrangement comprising:
         a magnetic sensor configured to sense the rotating magnetic field; and
         a transducer array configured to detect the rotating acoustic beam; and
      an energy source configured to direct energy to a target tissue that is offset from the energy guide apparatus;
   wherein the transducer array is also configured to operate in low-intensity imaging mode to generate an image of the energy guide apparatus; and
   wherein the localizing arrangement is configured to localize the energy guide apparatus within a body lumen using at least the generated image and the detected rotating acoustic beam.

2. The apparatus of claim 1, wherein the offset comprises a distance between the energy guide apparatus and a wall of the body lumen plus a distance between the wall of the body lumen and the target tissue.

3. The apparatus of claim 1, wherein the body lumen is a renal artery and the offset comprises a distance between the energy guide apparatus and a wall of the renal artery plus a distance between the renal artery wall and the target tissue.

4. The apparatus of claim 1, wherein:
   the energy guide apparatus comprises one or more radiopaque markers; and
   the localizing arrangement comprises a CT scanner configured to generate a CT image of the radiopaque markers, the localizing arrangement configured to localize the energy guide apparatus within the body lumen using at least the generated CT image.

5. The apparatus of claim 1, comprising a support structure provided at the distal end of the shaft and transformable between an introduction configuration and a deployed configuration, the support structure serving to maintain a position of the energy guide apparatus within the body lumen when in the deployed configuration.

6. An apparatus, comprising:
   an internal system comprising:
      a flexible shaft having a proximal end and a distal end; and
      an energy guide apparatus provided at the distal end of the shaft comprising a magnetic field generator configured to generate a rotating magnetic field and an acoustic transducer configured to generate a rotating acoustic beam; and
   an external system comprising:
      an array of sensors configured to sense the rotating magnetic field;
      an array of ultrasound transducers configured to detect the rotating acoustic beam and operable in a low-intensity imaging mode to generate an image of the energy guide apparatus;

a processor configured to localize the energy guide apparatus within a body lumen based at least on the generated image and the detected rotating acoustic beam; and an energy source configured to direct energy to a target tissue that is offset from the energy guide apparatus.

7. The apparatus of claim 6, wherein the offset comprises a distance between the energy guide apparatus and a wall of the body lumen plus a distance between the wall of the body lumen and the target tissue.

8. The apparatus of claim 6, wherein the body lumen is a renal artery and the offset comprises a distance between the energy guide apparatus and a wall of the renal artery plus a distance between the renal artery wall and the target tissue.

9. The apparatus of claim 7, wherein:
the acoustic transducer is configured to generate a signal indicative of the distance between the energy guide apparatus and the wall of the body lumen.

10. The apparatus of claim 6, wherein:
the array of sensors and the array of ultrasound transducers define a first reference frame used by the processor to localize the energy guide apparatus;
the energy source defines a second reference frame; and
the first reference frame is in a fixed measured relationship with respect to the second reference frame.

11. The apparatus of claim 6, wherein the energy source comprises a high intensity focused ultrasound array.

12. The apparatus of claim 6, wherein
the array of sensors and the array of ultrasound transducers comprise:
a plurality of magnetic field sensors configured to sense the rotating magnetic field; and
a plurality of acoustic receivers configured to detect the rotating acoustic beam.

13. The apparatus of claim 12, wherein:
the array of sensors and the array of ultrasound transducers define a first reference frame used by the processor to localize the energy guide apparatus;
the energy source defines a second reference frame; and
the first reference frame is in a fixed measured relationship with respect to the second reference frame.

14. The apparatus of claim 6:
wherein the magnetic field generator is configured to generate the rotating magnetic field at a target frequency;
wherein the energy guide apparatus further comprises a reflector arranged for rotation by the magnetic field generator; and
wherein the acoustic transducer is arranged to emit acoustic energy at the rotatable reflector for generating the rotating acoustic beam.

15. The apparatus of claim 14, wherein the array of sensors comprises magnetic field sensors configured to sense the rotating magnetic field at the target frequency.

16. The apparatus of claim 12, wherein the energy guide apparatus comprises one or more radiopaque markers and the external system comprises a radiopaque marker scanner.

17. An apparatus, comprising:
an in vivo apparatus comprising:
a flexible shaft having a proximal end and a distal end; and
an energy guide apparatus provided at the distal end of the shaft comprising:
a magnetic field generator configured to generate a rotating magnetic field; and
an ultrasound generator configured to generate a rotating acoustic beam; and
an ex vivo apparatus, comprising:
magnetic field sensors configured to sense the rotating magnetic field;
ultrasound transducers configured to detect the rotating acoustic beam;
a processor configured to localize the energy guide apparatus within a body lumen using the energy guide apparatus and based at least in part on an image of the energy guide apparatus generated by the ultrasound transducers in a low-intensity imaging mode and the detected rotating acoustic beam; and
an energy source configured to direct energy to a target tissue that is offset from the energy guide apparatus.

18. The apparatus of claim 17, wherein the energy source is configured to direct energy at two or more positions in the target tissue about a circumference of the energy guide apparatus.

19. The apparatus of claim 17, comprising a support structure provided at the distal end of the shaft and transformable between a configuration for introduction into the body lumen and a configuration for deployment in contact with a wall of the body lumen.

20. The apparatus of claim 19, wherein the body lumen is a renal artery and the target tissue is perivascular renal nerve tissue, and the offset comprises a distance between the energy guide apparatus and the renal artery wall plus a distance between the renal artery wall and the perivascular renal nerve tissue.

* * * * *